United States Patent
Bathelet

(10) Patent No.: US 9,803,974 B2
(45) Date of Patent: Oct. 31, 2017

(54) METHOD AND INSTALLATION FOR MEASURING THE GLASS DISTRIBUTION IN CONTAINERS

(71) Applicant: MSC & SGCC, Vourles (FR)

(72) Inventor: Guillaume Bathelet, Marcy L'Etoile (FR)

(73) Assignee: MSC & SGCC, Vourles (FR)

( * ) Notice: Subject to any disclaimer, the term of this patent is extended or adjusted under 35 U.S.C. 154(b) by 70 days.

(21) Appl. No.: 14/387,641

(22) PCT Filed: Mar. 27, 2013

(86) PCT No.: PCT/FR2013/050664
§ 371 (c)(1),
(2) Date: Sep. 24, 2014

(87) PCT Pub. No.: WO2013/144509
PCT Pub. Date: Oct. 3, 2013

(65) Prior Publication Data
US 2015/0076353 A1 Mar. 19, 2015

(30) Foreign Application Priority Data
Mar. 27, 2012 (FR) .................................. 12 52730

(51) Int. Cl.
*G01B 11/06* (2006.01)
*G01N 33/38* (2006.01)
(Continued)

(52) U.S. Cl.
CPC ............ *G01B 11/06* (2013.01); *B07C 5/3408* (2013.01); *G01N 21/90* (2013.01); *G01N 33/386* (2013.01)

(58) Field of Classification Search
CPC .............................. G01B 11/06; G01N 33/386
(Continued)

(56) References Cited

U.S. PATENT DOCUMENTS 3,535,522 A    10/1970   Green
3,721,501 A *   3/1973   Atkinson et al. ............. 356/432
(Continued)

FOREIGN PATENT DOCUMENTS

EP    0 643 297    3/1995
EP    0 679 883    11/1995
(Continued)

*Primary Examiner* — David Porta
*Assistant Examiner* — Djura Malevic
(74) *Attorney, Agent, or Firm* — Clark & Brody

(57) ABSTRACT

A method for measuring the distribution of the thickness of glass in glass containers at a high temperature comprises:
selecting at least one inspection area of the containers, so that the thickness relationship of the glass as a function of the infrared radiation intensity is homogeneous over the whole inspection area,
measuring, for each inspection area the glass thickness of the container in at least one movement point belonging to the inspection area, by means of a contactless point-like thickness measurement system,
measuring by means of a sensor sensitive to infrared radiation, which is emitted by the container,
determining, for each inspection area, a relationship between the measurement of the thickness taken at the measurement point and the infrared radiation,
and from the relationship and the relevant infrared radiation of each inspection area, determining the glass distribution of the container over each inspection area.

16 Claims, 3 Drawing Sheets

(51) Int. Cl.
*G01N 21/90* (2006.01)
*B07C 5/34* (2006.01)

(58) Field of Classification Search
USPC .............................................. 250/340, 338.1
See application file for complete search history.

(56) References Cited

U.S. PATENT DOCUMENTS

| | | | | |
|---|---|---|---|---|
| 3,729,632 A * | 4/1973 | Cho et al. | ........................ | 378/56 |
| 3,827,812 A * | 8/1974 | Heimann | .................... | 356/239.4 |
| 4,304,995 A * | 12/1981 | Huttunen et al. | ......... | 250/339.06 |
| 4,393,305 A * | 7/1983 | Shimizu et al. | ............ | 250/358.1 |
| 5,139,406 A * | 8/1992 | Hoshino et al. | .............. | 425/140 |
| 5,291,271 A * | 3/1994 | Juvinall et al. | ................. | 356/632 |
| 5,444,237 A * | 8/1995 | Takizawa | .................... | 250/223 B |
| 5,536,935 A * | 7/1996 | Klotzsch et al. | .......... | 250/223 B |
| 5,583,337 A * | 12/1996 | Chan | ............................ | 250/330 |
| 5,902,526 A * | 5/1999 | Davis et al. | ................. | 264/40.1 |
| 6,089,108 A * | 7/2000 | Lucas | .......................... | 73/865.8 |
| 6,188,079 B1 * | 2/2001 | Juvinall et al. | ........... | 250/559.27 |
| 6,192,101 B1 * | 2/2001 | Grodzins | ........................ | 378/55 |
| 6,198,102 B1 * | 3/2001 | Shepherd | ...................... | 250/340 |
| 6,424,414 B1 * | 7/2002 | Weiland et al. | ............ | 356/239.4 |
| 6,863,860 B1 * | 3/2005 | Birckbichler et al. | ........ | 264/410 |
| 6,872,895 B2 * | 3/2005 | Cochran et al. | .................. | 177/1 |
| 6,894,775 B1 * | 5/2005 | Cech | ......................... | 356/239.1 |
| 6,985,221 B2 * | 1/2006 | Semersky et al. | .......... | 356/239.6 |
| 7,020,324 B2 * | 3/2006 | Freifeld | ........................ | 382/152 |
| 7,098,440 B2 * | 8/2006 | Bathelet et al. | ............. | 250/221 |
| 7,271,893 B2 * | 9/2007 | Seethaler | .................... | 356/239.6 |
| 7,307,740 B2 * | 12/2007 | Lamy et al. | ................... | 356/632 |
| 7,354,538 B2 * | 4/2008 | Semersky et al. | ........... | 264/40.1 |
| 7,432,453 B2 * | 10/2008 | Cochran et al. | .................. | 177/1 |
| 7,595,870 B2 * | 9/2009 | Ringlien | .................... | 356/239.4 |
| 7,780,898 B2 * | 8/2010 | Birckbichler et al. | ........ | 264/408 |
| 7,858,942 B2 * | 12/2010 | Ott et al. | ................... | 250/358.1 |
| 7,924,421 B2 * | 4/2011 | Schmidt et al. | ............. | 356/239.4 |
| 8,208,141 B2 * | 6/2012 | Schmidt et al. | ............. | 356/402 |
| 8,525,114 B2 * | 9/2013 | Schabron | ................. | 250/339.12 |
| 9,036,023 B2 * | 5/2015 | Holtkamp et al. | .............. | 348/86 |
| 2003/0223086 A1 * | 12/2003 | Semersky et al. | ............ | 356/630 |
| 2006/0012804 A1 * | 1/2006 | Wilke et al. | ................. | 356/632 |
| 2006/0208172 A1 * | 9/2006 | Akkerman et al. | ........ | 250/223 B |
| 2007/0295922 A1 * | 12/2007 | Ringlien | ................. | 250/559.44 |
| 2008/0197542 A1 * | 8/2008 | Birckbichler et al. | ........ | 264/410 |
| 2011/0141265 A1 * | 6/2011 | Holtkamp et al. | .............. | 348/86 |

FOREIGN PATENT DOCUMENTS

| | | | | |
|---|---|---|---|---|
| EP | 1 020 703 | | 7/2000 | |
| EP | 1020703 A2 * | | 7/2000 | ............ G01B 11/06 |
| EP | 2063219 A1 * | | 5/2009 | |
| FR | 2 751 068 | | 1/1998 | |
| WO | WO 2011137264 A1 * | | 11/2011 | |

* cited by examiner

METHOD AND INSTALLATION FOR MEASURING THE GLASS DISTRIBUTION IN CONTAINERS

The present invention relates to the technical field of inspecting containers or translucent or transparent hollow objects having a high temperature.

The object of the invention is more specifically directed to the high rate inspection of objects such as glass bottles or flasks leaving a shaping manufacturing machine.

In the preferred field of the manufacturing of glass containers, the use of the infrared radiation emitted by the containers upon leaving the shaping machine is known in order to achieve a check or an inspection with view to detecting possible defects on the surface or inside the containers. This is notably the case of patent EP 0 679 883. The quality control of such containers gives the possibility of removing those which have defects which may affect their aesthetical aspect or more seriously, become a real risk for this subsequent uses. Thus, it appears to be necessary to control the quality of the thickness distribution of such containers in order to remove the containers having too small thicknesses or differences in thicknesses in certain areas which may affect the mechanical strength.

Conventionally, the shaping machine consists of different cavities each equipped with a mold in which the container assumes its final shape at high temperature. Upon leaving the shaping machine, the containers are conveyed so as to form a queue on a transport conveyor successively bringing the containers so that they may pass into various treatment stations such as spraying and annealing stations.

It appears to be of interest to identify a shaping defect as soon as possible upon leaving the shaping machine before the various treatments stations in order to be able to correct it as early as possible at the shaping machine. In the state of the art, various solutions have been proposed for inspecting containers at high temperature leaving a shaping machine with view to measuring the distribution of the glass of such containers.

For example, U.S. Pat. No. 3,535,522 describes a method for measuring the glass thickness of a container consisting of measuring the infrared radiation emitted by such a container upon leaving the shaping machine. The measurement of the infrared radiation is conducted while the container is placed in an oven in order to homogenize the temperature of the container to a determined value. This technique does not allow continuous monitoring of the containers and requires handling of the containers leading to a slow process and which may cause deformations of the containers.

Patent EP 0 643 297 describes a device giving the possibility of carrying out an analysis and diagnostic on a method for manufacturing glass products including a sensor sensitive to the infrared radiation emitted by the objects leaving the shaping machine. This system also includes a digital processing device resorting to the application of a mathematical reference model in order to determine the deviations existing in the distribution of the glass and the causes leading to the presence of thermal constraints in the container.

In practice it seems difficult or even impossible to apply such a technique insofar the mathematical model is extremely complex to apply since the measurement of the infrared radiation depends on many parameters such as those listed as a non-limiting example hereafter:

the intensity of the infrared radiation emitted by the hot containers strongly depends on temperature according to the Stefan Boltzmann law:

$E = sT^4$ wherein:

E=equals total amount of radiation emitted by an object in (watts m$^{-2}$)

s=equals the Stefan Boltzmann constant=5.67×10$^{-8}$ Watts m$^{-2}$K$^{-4}$

T=the temperature in degrees Kelvin (K).

Thus, the intensity of the infrared radiation is not a simple linear function of temperature. Further it depends on the wavelengths.

During the shaping operation, the wall of the container is cooled by contact with the mold on its external surface and by blowing air on its internal surface. Fast cooling generates significant thermal inhomogeneities in the material, between the internal and the external surfaces of the container. The emission of the infrared radiation is therefore the integration of a heat distribution in the thickness of the container. The infrared emission in each point of the surface is therefore complex to apprehend.

The intensity of the infrared radiation emitted by the hot containers depends on the characteristics of these hot containers such as for example, the size, color, shape and composition of the glass.

It should be considered that the distance between the infrared sensor and the outlet of the molds is different from one mold to the other so that the cooling time for each hot container is different, so that the hot containers have different temperatures when they pass in front of the infrared sensor.

In other words, the intensity of the infrared radiation measured by the sensor depends on the origin of the manufacturing mold and more specifically on the position of this mold relatively to the sensor.

At the outlet of the shaping machine, the containers are placed by sliding them onto a conveyor. The result is a difference in the positioning of the containers on the conveyor relatively to the infrared measurement sensor, which may modify the measurement made.

From the foregoing, the result is that many parameters influence the infrared radiation so that such a patent does not provide a solution for measuring the distribution of the glass thickness for high temperature containers. This patent simply teaches how to determine deviations in the distribution of the glass i.e. relative thickness values between different regions of the containers. This patent does not give the possibility of measuring the absolute value of the glass thickness of the containers.

According to an alternative embodiment, this patent provides the application of an optical sensor with which it is possible to produce images of the glass products in order to obtain information on deviations and/or on the distribution of the glass. The information is compared with the data obtained from the sensor sensitive to the infrared radiation so as to be able to adjust the criteria according to which the data provided by the sensor sensitive to the infrared radiation were analyzed. If the application of this alternative embodiment provides a correction to the criteria used, it does not give a possibility of finding a remedy to the drawbacks inherent to the method described in this patent and recalled above. Also this solution does not allow measurement of the thickness of the glass in absolute value and consequently the distribution of the thickness over an extended area and even less over the whole container.

Patent applications EP 1 020 703, US 2006/0012804 and FR 2 751 068 describes various techniques for contactless measurement of the thickness of glass products having a high temperature. These point-like techniques are not suitable for measuring the distribution of the thickness of the glass over a large surface of containers running at a high rate in front of the measurement station.

The present invention aims at finding a remedy to the drawbacks of the prior techniques by proposing a method allowing measurement of the distribution of the thickness of the glass in hot glass containers leaving shaping cavities, the method being simple to apply while allowing accurate measurements of the distribution of the thicknesses of the glass in containers.

In order to achieve such an object, the method for measuring the distribution of the thickness of the glass in glass containers at a high temperature leaving shaping cavities, aims at applying at least one sensor sensitive to the infrared radiation emitted by the containers, suitable for obtaining an image of the distribution of the infrared radiation. The method includes the following steps:

selecting at least one area for inspecting the container, so that the glass thickness relationship as a function of the intensity of the infrared radiation is homogeneous over the whole of this inspection area, measuring for each inspection area, the glass thickness of the container in at least one measurement point belonging to the inspection area, by means of a contactless point-like system for measuring thickness, measuring by means of a sensor sensitive to the infrared radiation, the distribution of the infrared radiation emitted by the container at least in each inspection area, determining, for each inspection area, a relationship between the measurement of the thickness taken at the measurement point and the relevant infrared radiation at said measurement point, and from said relationship and from the distribution of the relevant infrared radiation on each inspection area, determining the glass distribution in the container over each inspection area.

The method according to the invention also includes in a combination, either one or both of the following additional features:

measuring the glass thickness of the container along a direction perpendicular to the surface of the container by means of the point-like measurement system, measuring the glass thickness of the container only along the different neighboring measurement points located along a portion of the section of the container and for which the thickness measurements are reliable, measuring the infrared radiation emitted by the container by its inspection area located on the front face of the container, using as a relationship between the thickness measurement and the infrared radiation, a mathematical model determined from one or several measurement points for the thickness and for the infrared radiation for each inspection area, selecting the inspection areas so that, for each inspection area, the parameters having an influence on the infrared radiation other than the glass thickness, each have substantially homogeneous values over the whole of said inspection area, selecting the inspection areas of the container so that for each inspection area, the shape and/or the surface condition of the container is substantially constant, selecting the inspection areas of the container so that for each inspection area, the slope of the container is substantially constant, selecting several inspection areas of the container so as to obtain by combination a partial or complete three-dimensional representation of the container, consisting of selecting an inspection area identical for all the containers or an inspection area which changes depending on the original cavities of the containers or an inspection area determined for each container according to the analysis of the infrared radiation, filtering the glass thickness measurement conducted by the contactless point-like measurement system and the measurement of the infrared radiation for removing the outlying measurement.

Another object of the invention also relates to an installation for measuring the distribution of the thickness of the glass in glass containers leaving shaping cavities, including at least one sensor sensitive to the infrared radiation emitted by the containers and allowing determination of a distribution of infrared radiation over at least one inspection area and connected to a control and processing unit. According to the invention, the installation includes at least one contactless point-like system for measuring thickness, suitable for measuring the glass thickness of the container along a direction perpendicular to the surface of the container, in at least one measurement point belonging to the inspection area, the point-like measurement system being connected to the processing unit which includes means for determining a relationship between the measurement of the thickness made at the measurement point and the relevant infrared radiation at said measurement point, and means for determining from said relationship and from the relevant infrared radiation on the inspection area, the glass distribution of the container over the inspection area.

The installation according to invention also includes in a combination, either one or both of the following additional features:

as a contactless point-like system for measuring thickness, a laser or confocal triangulation system with color coding, a sensor sensitive to the infrared radiation, including an objective for which the field depth is adapted so that the infrared radiation received from the rear face of the container opposite to the front face on which the inspection area is defined, is homogeneous, a series of point-like thickness measurement systems located in a plane substantially perpendicular to the direction of motion of the containers in front of said point-like thickness measurement systems, the point-like system measuring the thickness of the container in points belonging to inspection areas having different tilts.

Various other characteristics emerge from the description made below with reference to the appended drawings which show, as non-limiting examples embodiments of the object of the invention.

Figure 1:
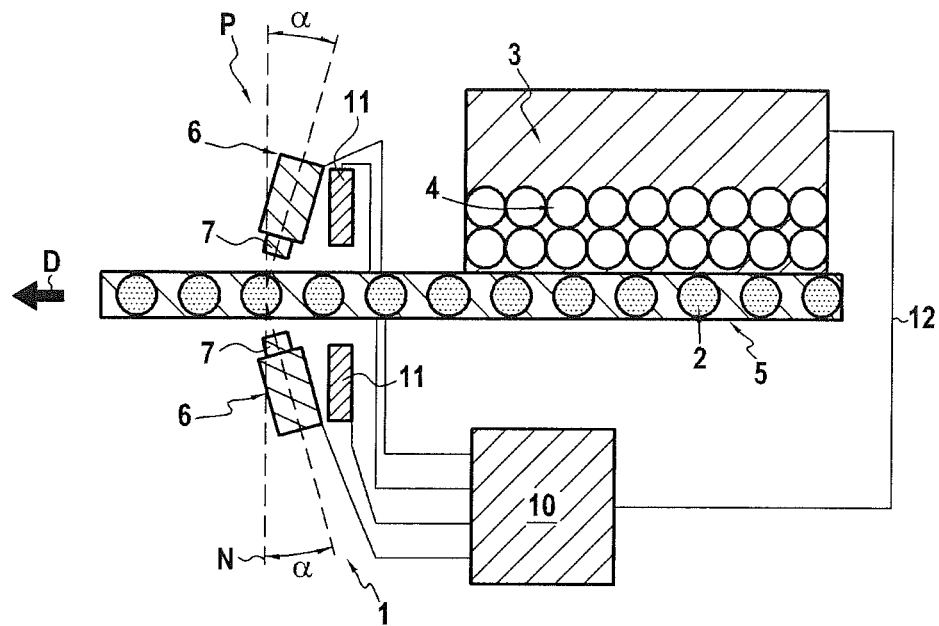
FIG. 1 is a schematic view of a measurement installation associated with a machine for shaping containers.
Figure 2:
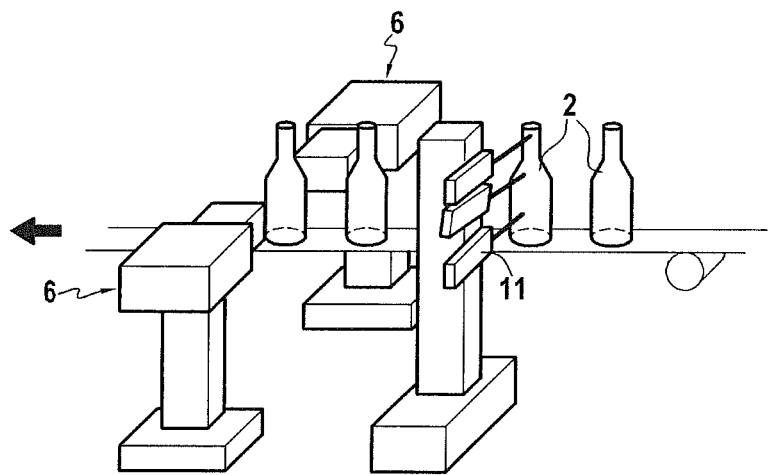
FIG. 2 is a schematic perspective view of a measurement installation according to the invention.

As this emerges more specifically from FIG. 1, the object of the invention relates to an installation 1 giving the possibility of measuring the distribution of the glass thickness in glass containers 2 such as bottles or flasks for example. The installation 1 is placed so as to allow measurements to be conducted while the container 2 leaving a manufacturing or shaping machine 3 has a high temperature, i.e. for example a temperature comprised between 450° C. and 550° C.

The shaping machine 3 conventionally includes a series of cavities 4 each providing the shaping of a container 2. In a known way, the containers 2 which have just been shaped by the machine 3 are conveyed on an outlet conveyor 5 so that the containers 2 form a queue on the conveyor 5 moving along the direction D. The containers 2 are then successively conveyed to different processing stations and in particular to the measurement installation 1 which is placed as close as possible to the shaping machine 3.

The installation 1 includes at least one and in the illustrated example two sensors 6 sensitive to the infrared radiation emitted by the containers 2 passing in front of each sensor 6. The sensors 6 are thus placed at the outlet of the shaping machine 3 so as to be sensitive to the infrared radiations emitted by the containers 2. In the illustrated example, both sensors 6 are positioned on either side of the conveyor 5 so as to allow both sides of the container 2 to be inspected. For example, each sensor 6 is formed by an infrared camera provided with an objective 7. According to an advantageous alternative embodiment, the inspection direction of each sensor 6 forms an angle alpha with the direction N perpendicular to the translation direction D. Preferably, the infrared image sensor is sensitive in the near infrared range.

The sensors 6 are connected to a unit 10 for monitoring and processing the output signals delivered by the sensors 6. The sensor 6 generates an output signal for example a video signal in response to the infrared radiation emitted by a container 2. The unit 10 is suitable for controlling the operation of the sensors 6 when a container 2 passes into their field of vision so that each sensor 6 takes at least one image of each of the containers 2 moving past at a high rate. The unit 10 is suitable for producing from the signals delivered by the sensor 6, images of the distribution of the infrared radiation emitted by the containers 2.

According to an advantageous alternative embodiment, the images taken by the sensor 6 sensitive to the infrared radiation are filtered in order to remove locally outlying values corresponding to particularities of the containers such as localized etchings or defects (surface accidents, foreign body, bubble).

The installation 1 according to the invention also includes at least one and in the illustrated example, six systems 11 ensuring contactless measurement of the thickness of the glass of the container 2, along a point-like or localized area as schematized on the drawings with point M. The measurement systems 11 considered as point-like in the following description are connected to the controlling and processing unit 10. Advantageously, each point-like measurement system 11 is positioned relatively to the container 2 so that its measurement axis is perpendicular to the surface of the container 2.

Each point-like measurement system 11 is of any type known per se in order to allow the measurement of the thickness of the glass of the container 2 having a high temperature. The point-like measurement system 11 is for example a laser system or a confocal triangulation system with color coding. Such a system 11 generally operates with a light source adapted according to the color of the containers 2. Advantageously, in order to avoid the system to be disrupted by the infrared radiation naturally emitted by the hot containers, a band pass filter centered on the color of the light source is added for the system operating by laser triangulation while a low pass filter is used for cutting off the infrared for the color measurement system.

Each point-like measurement system 11 gives the possibility of obtaining absolute thickness measurements of the glass according to the metric system. Thus, it is possible to determine the thickness of the glass with an accuracy, for example of the order of a tenth of a mm.

According to an advantageous feature of the embodiment, the measurements taken by the point-like thickness measurement systems are filtered for removing the outlying measurements either corresponding to particularities of the containers such as localized etchings or faults, or to handling random faults, or finally any disruption of the signal of electric or electro-magnetic origin.

The application of the measurement installation 1 directly results from the measurement method according to the invention which is described hereafter.

Figure 3:
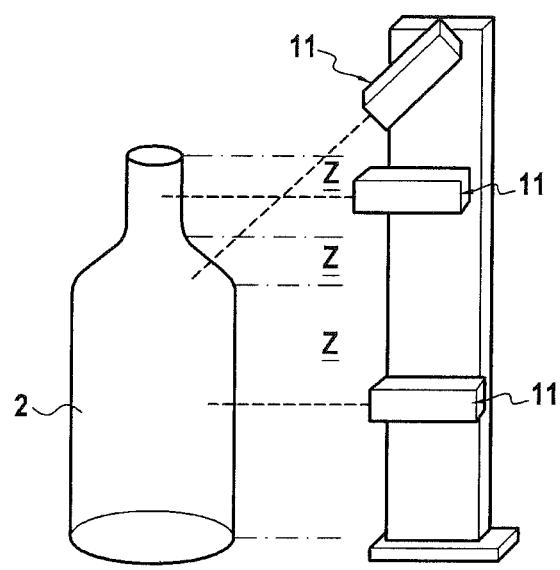
FIG. 3 is a schematic perspective view of the measurement installation according to the invention, illustrating an arrangement of point-like thickness measurement systems.

The measurement method, as this emerges more specifically from FIG. 3, consists of selecting at least one inspection area Z of the container 2 for which the thickness distribution of the glass is to be measured. The inspection area Z is selected so that the glass thickness relationship as a function of the infrared radiation is homogeneous over the whole of this inspection area Z. Also, in order to measure the distribution of the glass thickness over the totality of the container, several inspection areas Z are selected.

Figure 3A:
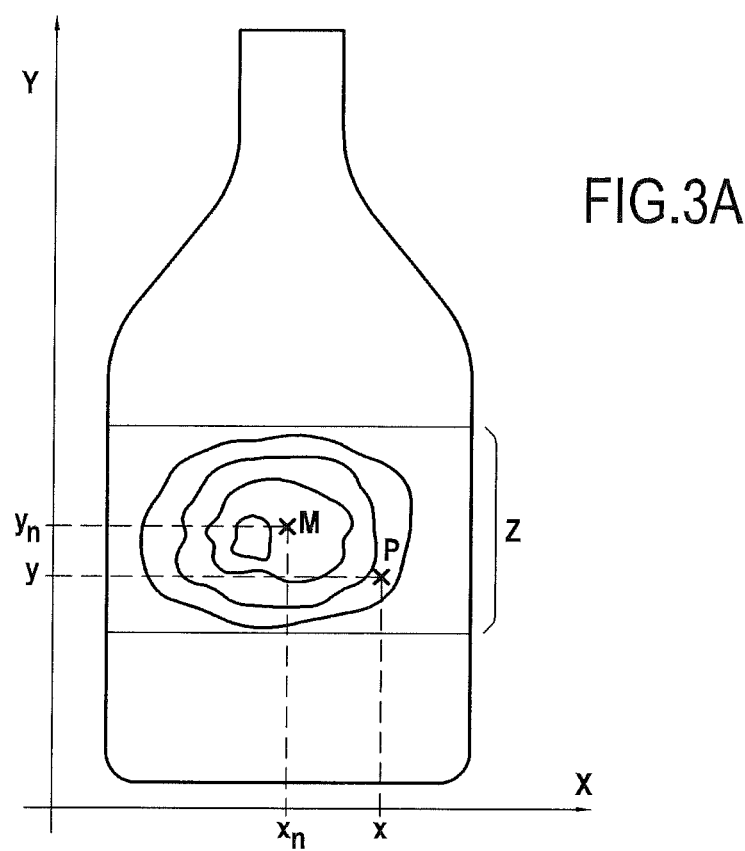
FIG. 3A is a schematic view explaining the selection of the inspection area for which the distribution of the glass is to be measured.

In a general way, each surface element of the container 2 assimilated to a point P in FIG. 3A, with coordinates x, y emits infrared radiation (x, y). It should be considered that the infrared radiation Ir(x, y) emitted in each point P(x, y) and for each wave length λ, mainly depends on the glass thickness E(x, y), on the temperature T(x, y), integrated over the whole of the thickness of the wall of the container 2, on the spectral absorption a(λ,x,y) of the material of the container, on the spectral reflection r(λ,x,y) of the material of the container, and on the shape and surface condition $F_0(x, y)$, on the container and in particular on the orientation of the emission surface relatively to the measurement direction.

In order to simplify the method, the assumption may be made that the composition of the material is homogeneous in at least each inspection area Z or even in the container 2 or in all the containers 2, so that the spectral absorption a(λ) and the spectral absorption r(λ) do not vary according to the position x and y.

The glass thickness E(x, y) of a container is therefore related to the infrared radiation through the approximate relationship (1) of the following type:

$$E(x,y)=F(Ir(x,y)),T(x,y),F_0(x,y),a(\lambda),r(\lambda))$$

According to an advantageous embodiment feature, each inspection area Z is selected so that the parameters having an influence of the infrared radiation Ir other than the glass thickness, each have substantially homogeneous values over the whole of said inspection area Z. In other words, from relationship (1), it is possible to formalize a simplified relationship such that E(x, y)=fz(Ir(x, y)) with fz being the simplified function, this relationship being constant in the whole inspection area Z for which each parameter T(x, y), $F_0(x, y)$, a(λ), r(λ) is homogeneous or determined a priori.

The method according to the invention is based on the assumption that the thickness relationship of the glass as a function of the intensity of the infrared radiation is not significantly modified in each of the inspection areas Z since the other parameters vary little. The specific simplified functions fz for each of the inspection areas are based on a mathematical model derived from mathematical modeling taking into account physical loads (thermodynamics, heat transfers by conduction and radiation, thermography of semi-transparent bodies) or by empirical modeling by means of abaca or experimental tables.

This simplified function fz may be described by a mathematical model such as for example an equation with partial derivatives. In this case, said mathematical model may be obtained by simplification of the function F.

According to an advantageous alternative of the method, the simplified function fz may be according to a single mathematical model for each area, only the parameters or coefficients vary according to the areas. Said coefficients are then calculated for each container for each area, from thickness measurements at the measurement point M.

According to another alternative of the method, the function fz may have a different expression for each area, for example depending on the shape known a priori of the container in the area (conical, cylindrical shape, square section). In this case, the function fz is different for each area, but nevertheless each parameter is recalculated for each container from thickness measurements at the measurement point M.

According to a third alternative, the simplified function fz is purely empirical and represented by abaca obtained by experiment. In this case, the point-like thickness measurements are used for selecting the operating points on said abaca, and the relationship between thickness and radiation results from the travel of the thereby selected abaca.

According to another alternative, the function fz is obtained from measurement of thicknesses of several points M distributed according to an areae covered by the thickness sensor during the displacement of the articles, which gives the possibility of either making the thickness measurement more reliable by averaging the measurements E(M) or further identifying several parameters of the simplified function fz when the latter is of a higher order.

Thus, according to the previous alternatives, a simplified function fz which is considered as constant in the whole of an inspection area Z may be different for another inspection area Z so that the simplified function fz is specific for each of the inspection areas Z.

It results from the foregoing description that the inspections area Z of the container 2 are selected so that for each inspection area Z, the shape and/or the surface condition of the container 2 are substantially constant. According to an advantageous alternative embodiment, the inspections area Z of the container 2 are selected so that each inspection area Z corresponds to a region of the wall of the container 2 for which the slope is substantially constant.

If the measurement of the distribution of the thickness of the glass has to be carried out over the whole height of the container 2, then the number of inspection areas 2 is related in the particular case to the number of slopes which the wall of the container 2 has. In the illustrated example, the container 2 has three inspection areas Z corresponding to the vertical body of the container, at the shoulder of the container having a smaller slope and at the neck of the container 2 having a strong slope. Advantageously, several inspection areas Z are selected so as to obtain by combination, a partial or complete three-dimensional representation of the container 2. In the illustrated example, the breaking down of the container into three areas, inspected on either side of the conveyor 5, gives the possibility of obtaining by a combination a complete three-dimensional representation of each container 2.

For each inspection area Z, the glass thickness of the container 2 is measured by means of a point-like thickness measurement system 11 in a measurement point M belonging to said measuring area Z. Preferably, the measurement point M is selected at the center of the measuring area. According to an advantageous characteristic of the invention, the thickness of the glass is measured by means of a point-like thickness measurement system 11, along a direction perpendicular to the surface of the container 2. Thus, in the case when the container 2 has a profile with three different slopes, the installation includes at least three point-like measurement systems 11. However in the illustrated example, the container 2 moves in translation past the measurement installation 1 so that for measuring the distribution of the thickness over the whole of the container, point-like thickness measurement systems 11 are provided so as to be available on either side of the plane of the movement of the containers. In the illustrated example, three point-like thickness measurement systems 11 are positioned on each side of the motion conveyor 5 in order to measure the thickness of the neck, of the shoulder and of the body of the container 2, respectively.

Figure 4:
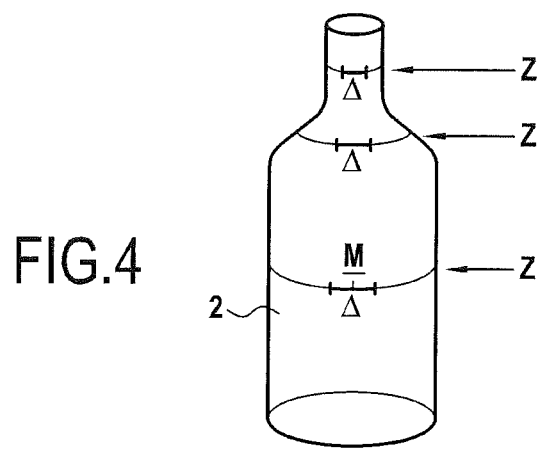
FIG. 4 is a view showing the time-dependent change in the thickness measurement on the circumference of a container.
Figure 5:
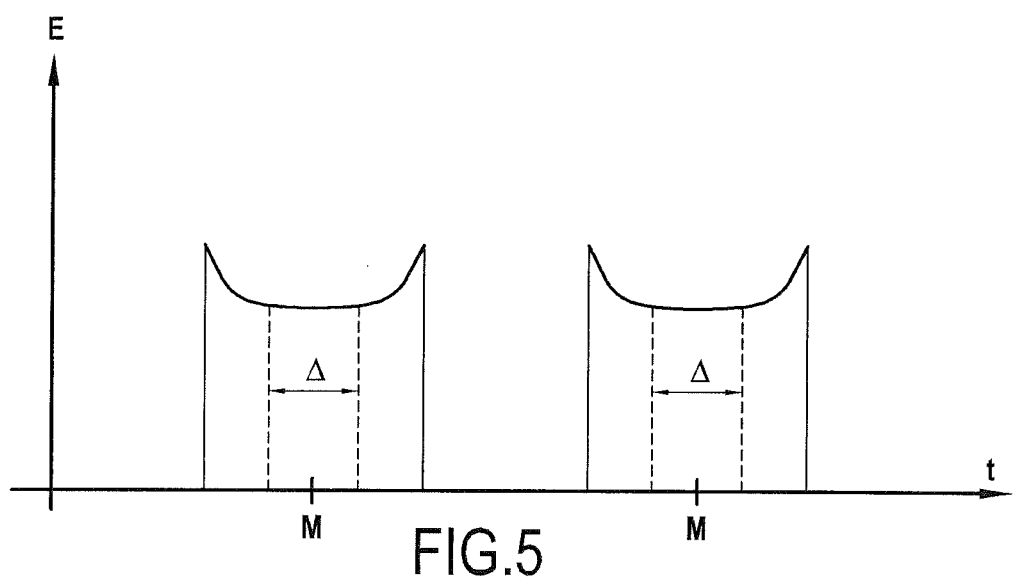
FIG. 5 is a diagram showing an example of the time-dependent change in the thickness measurement over time, during the successive passing of two containers in the measurement field of a point-like thickness measurement system.

As explained above, each container 2 moves past the point-like measurement system 11 so that the thickness measurement E changes according to the position on the container 2 relatively to the point-like measurement system 11 (FIGS. 4 and 5). The control and processing unit 10 is adapted so as to remove the outlying measurements of the thickness E which appear beyond a determined angle between the measurement direction of the point-like measurement system 11 and the normal to the surface of the container 2. The control and processing unit 10 gives the possibility of determining, from thickness measurements E, the position of the point M of the surface of the container for which preferably the normal coincides with the measurement direction of the point-like measurement system 11. Of course, the control and processing unit 10 is able to take into account the measurements of thicknesses in different points neighboring the point M, located along a portion A of the section of the container 2 and for which the thickness measurements are reliable because of the orthogonality of the surface to the measurement direction and/or of the presence of the measured wall in the measurement area of the sensor, and/or the absence of artifacts or fault or etchings.

It should be considered that the instantaneous thickness measurements are considered as being point-like in the sense that the measurement area is small relatively to the inspection area Z. For example, the measurement area of the thickness of the glass corresponds to the size of the pixel of the images of the distribution of the infrared radiation, i.e. for example less than 1 mm$^2$ for a container 2 with a diameter of 100 mm.

The method according to the invention also consists of measuring by means of the sensor sensitive to infrared radiation 6, the infrared radiation emitted by each container 2 in each of the selected inspection areas Z.

The method consists of determining for each container 2 and for each inspection area Z, a relationship between the thickness measurement E taken at the measurement point M, i.e. E(M), and the relevant infrared radiation at said measurement point M i.e. Ir(M). In other words, the thickness measurement delivered by the point-like measurement sensor 11 is used for calibrating each inspection area Z and for each container 2. From this relationship E=fz(Ir) and from the distribution of the relevant infrared radiation Ir(x,y) over the extent of each inspection area Z, the method gives the possibility of determining the distribution of the thickness (E(x,y)) of the container over said inspection area Z.

Such a method thus allows accurate determination of the distribution of the thickness of the gas for each container 2. This method notably gives the possibility of ignoring:
- the color of the glass since the transmission and the color variation of the glass are taken into account by the calibration through the thickness measurement,
- the orientation of the containers since the thickness and infrared radiation measurements are synchronized,
- temperature variations over time of the containers 2 in so far that each inspection area is selected so as to be homogeneous in temperature and that the function E=fz(Ir) or at least its parameters are recalculated for each article. This cutting out into inspection areas Z may result from an experiment and/or from mathematical modeling, from a sampling measurement or a continuous measurement, by means of temperature sensors (pyrometer or thermographic camera).

According to another advantageous embodiment feature, the method consists of measuring the distribution of the infrared radiation emitted by an inspection area Z located on the front face of the container 2. For this purpose, each sensor sensitive to infrared radiation 6 includes an objective 7, the field depth of which is adapted so that the distribution of the infrared radiation of the rear face of the container opposite to the front face on which the inspection area is defined, is uniform. In other words, the measurement error which may be generated by the radiation variations from the rear face of the container 2 is suppressed.

According to an alternative embodiment, the inspection area Z of the container taken into account is identical for all the identical containers of the same production. According to another embodiment, the inspection area Z taken into account changes according to the original cavities 4 of the containers. Thus, the same inspection area Z may be taken into account for all the containers coming from the same original cavity 4. According to another embodiment, the inspection area Z is determined for each container depending on the analysis of the infrared radiation.

The invention is not limited to the described and illustrated examples since various modifications may be provided thereto without departing from its scope.

The invention claimed is:

1. A method for measuring a distribution of a thickness of glass in glass containers (2) at a high temperature leaving shaping cavities (4), the method applying at least one sensor sensitive to infrared radiation (6) emitted by the containers (2) suitable for producing an image of a distribution of the infrared radiation, characterized in that the containers pass in translation direction (D) in front of at least said sensor sensitive to the infrared radiation (6) and in front of at least one contactless point-like thickness measurement system (11) and in that the method includes for each container the following steps:
   selecting at least one inspection area (Z) of the container (2) so that for each inspection area (Z):
   a temperature of a wall of the container has a homogeneous value over a whole of said inspection area;
   a shape of the container and a surface condition of the container has homogeneous values over the whole of said inspection area;
   a spectral absorption of a material of the container has a homogeneous value over the whole of said inspection area;
   a spectral reflection of the material of the container has a homogenous value over the whole of said inspection area;
   formalizing a simplified function fz such that E(x, y)=fz (Ir(x, y), E(x, y) being the glass thickness at a point P and Ir(x, y) being the infrared radiation at the point P,
   measuring, for each inspection area (Z), an absolute glass thickness of the container according to the metric system in at least one measurement point (P) belonging to the inspection area (Z), by means of the contactless point-like thickness measurement system (11),
   measuring by means of the sensor sensitive to infrared radiation (6), the distribution of the infrared radiation Ir emitted by the container (2) at least in each inspection area (Z),
   determining, for each container and for each inspection area (Z), a relationship between the measurement of the thickness taken at the measurement point and relevant infrared radiation at said measurement point, said relationship being such that E(x, y)=fz(Ir(x, y)), fz being the simplified function, and E(x, y) the absolute glass thickness measured at the point P by the contactless point-like thickness measurement system (11) and Ir(x, y) being the infrared radiation measured at the point P,
   and from said relationship E(x, y)=fz(Ir(x, y)) and from the distribution of the relevant infrared radiation of each inspection area, determining the distribution of the glass thickness of the container of each inspection area (Z).

2. The method according to claim 1, further comprising measuring the glass thickness of the container (2) along a direction perpendicular to the surface of the container by means of the contactless point-like measurement system.

3. The method according to claim 1, further comprising measuring the glass thickness of the container (2) in different neighboring measurement points located along a portion (Δ) of a section of the container (2), for which the measurements of thicknesses are reliable.

4. The method according to claim 1, further comprising measuring the infrared radiation emitted by the container (2), by each inspection area (Z) located on a front face of the container taken relatively to the sensor sensitive to infrared radiation (6).

5. The method according to claim 1, further comprising using as a relationship between the thickness measurement and the infrared radiation, a mathematical model determined from one or several thickness measurement points and from the infrared radiation for each inspection area (Z).

6. The method according to claim 1, further comprising selecting the inspection area (Z) of the container so that for each inspection area (Z), the shape and/or the surface condition of the container is substantially constant.

7. The method according to claim 1, further comprising selecting the inspection areas (Z) of the container so that for each inspection area (Z) a slope of the container is substantially constant.

8. The method according to claim 1, further comprising selecting several inspection areas (Z) of the container (2) so as to obtain by combination a partial or complete three-dimensional representation of the container.

9. The method according to claim 1, further comprising selecting an inspection area (Z) identical for all the containers or an inspection area (Z) which changes according to original cavities (4) of the containers or an inspection area (Z) determined for each container depending on an analysis of the infrared radiation.

10. The method according to claim 1, further comprising filtering the glass thickness measurement conducted by the contactless point-like thickness measurement system (11) and the infrared radiation measurement for suppressing outlying measurements.

11. The method according to claim 1, wherein the contactless point-like thickness measurement system is a light source.

12. The method of claim 1, further comprising providing a control and processing unit (10) to perform said determining of the distribution of the glass thickness of the container of each inspection area.

13. An installation for measuring a distribution of a thickness of glass in glass containers (2) leaving shaping cavities (4), a conveyor (5) moving the containers in translation direction (D) in front of at least one sensor (6) sensitive to infrared radiation emitted by the containers and in front of at least one contactless point-like thickness measurement system (11), the sensor sensitive to infrared radiation (6) allowing determination of a distribution of infrared radiation over at least one inspection area (Z) and being connected to a control and processing unit (10), characterized in that the control and processing unit (10) includes the one contactless point-like thickness measurement system (11), suitable for measuring an absolute glass thickness of the container according to the metric system along a direction perpendicular to a surface of the container, in at least one measurement point (P) belonging to the inspection area (Z), the parameters being:

a temperature of a wall of the container has a homogeneous value over a whole of said inspection area, a shape of the container and a surface condition of the container has homogeneous values over the whole of said inspection area, a spectral absorption of a material of the container has a homogeneous value over the whole of said inspection area, a spectral reflection of the material of the container has a homogenous value over the whole of said inspection area, the contactless point-like thickness measurement system (11) being connected to the processing unit (10) which includes means for determining a relationship between a measurement of the thickness taken at the measurement point and relevant infrared radiation at said measurement point, said relationship being such that $E(x, y)=fz(Ir(x, y))$, fz being the simplified function, and $E(x, y)$ the absolute glass thickness measured at the point P by the contactless point-like thickness measurement system (11) and $Ir(x, y)$ being the infrared radiation measured at the point P, and means for determining from said relationship $E(x, y)=fz(Ir(x, y))$, and from the relevant infrared radiation on the inspection area, the distribution of the glass thickness of the container all over the inspection area.

14. The measurement installation according to claim 13, further comprising as the contactless point-like thickness measurement system (11) a laser triangulation or confocal system with color coding.

15. The measurement installation according to claim 13, characterized in that the sensor sensitive to the infrared radiation (6) includes an objective (7) for which a field depth is adapted so that the infrared radiation received from a rear face of the container (2) opposite to a front face on which the inspection area (Z) is defined, is homogeneous.

16. The measurement installation according to claim 13, further comprising at least one series of contactless point-like thickness measurement systems (11) located in a plane substantially perpendicular to a direction of the containers moving past said contactless point-like thickness measurement systems, the contactless point-like thickness measurement system (11) measuring the thickness of the container at points belonging to inspection areas (Z) having different tilts.

* * * * *